United States Patent [19]
Reynolds

[11] Patent Number: 5,932,284
[45] Date of Patent: Aug. 3, 1999

[54] METHOD OF APPLYING ADHESIVE TO AN EDGE OF MOVING WEB

[75] Inventor: Gary Mack Reynolds, Neenah, Wis.

[73] Assignee: Kimberly-Clark Worldwide, Inc., Neenah, Wis.

[21] Appl. No.: 08/932,888

[22] Filed: Sep. 15, 1997

Related U.S. Application Data

[63] Continuation of application No. 08/729,109, Oct. 11, 1996, abandoned.

[51] Int. Cl.⁶ ........................................................ B05D 5/10
[52] U.S. Cl. ..................................... 427/207.1; 427/208.2; 427/208.4; 427/208.6; 427/284; 427/285; 427/424
[58] Field of Search ..................................... 427/284, 285, 427/207.1, 208.2, 208.4, 208.6, 424

[56] References Cited

U.S. PATENT DOCUMENTS

| | | | |
|---|---|---|---|
| 1,840,052 | 1/1932 | O'Donnell | 427/285 X |
| 4,949,668 | 8/1990 | Heindel et al. | 118/314 |
| 4,968,534 | 11/1990 | Bogardy | 427/282 |
| 5,094,886 | 3/1992 | Bogardy | 427/282 |
| 5,342,647 | 8/1994 | Heindel et al. | 427/2.31 |
| 5,415,717 | 5/1995 | Perneborn | 156/276 |
| 5,501,149 | 3/1996 | Schleinz et al. | 101/416.1 |

FOREIGN PATENT DOCUMENTS

| | | |
|---|---|---|
| 0 293 065 A2 | 11/1988 | European Pat. Off. . |
| 40 04879 A1 | 8/1990 | Germany . |
| WO 95/00092 | 5/1995 | WIPO . |

Primary Examiner—Bernard Pianalto
Attorney, Agent, or Firm—Michael L. Winkelman; Jerry F. Janssen; Brian R. Tumm

[57] ABSTRACT

The invention relates to methods of applying adhesive to a lateral edge of a first web. The method includes transporting the first web along a first path and transporting a second web along a second path generally in surface-to-surface relationship with the first web at the lateral edge, with the second web extending outwardly from the first web. When adhesive is applied such as by spraying to the first web at the lateral edge, at least some adhesive passes outwardly of the lateral edge as overspray and is received by the second web. Thus, adhesive applied to the edge of the first web is received in combination by both of the first and second webs. Both of the first and second webs can be utilized in manufacturing articles. In some embodiments, adhesive is applied at both first and second lateral edges of the first web. In some embodiments, spaced leg cutouts are formed in lateral edges of the web. In this context, second and optionally third webs can receive adhesive overspray directed toward the first web including at locations of the leg cut-outs. The second web can have a width greater than the first web and can thus extend outwardly beyond at least both leg cut-outs of the first web, and preferably beyond the entire lengths of the lateral edges of the first web.

38 Claims, 5 Drawing Sheets

FIG. 5

METHOD OF APPLYING ADHESIVE TO AN EDGE OF MOVING WEB

This application is a continuation, of application Ser. No. 08/729,109 filed Oct. 11, 1996, now abandoned.

FIELD OF THE INVENTION

This invention relates to a method of applying adhesive to the edge of a moving first web of material. A second web of material underlies the first web and receives excess adhesive placed beyond the edge of the first web. The method allows placement of adhesive to the edge of the first web without forming angel hairs or having the adhesive otherwise string out. The method prevents contamination of equipment.

BACKGROUND OF THE INVENTION

One method of applying adhesive to the edge of a moving web is to simply spray adhesive onto the edge of the web. Any adhesive not received and retained by the web, namely the overspray, can contaminate equipment. Further, adhesive disposed at the distal edge of the web can string out and form angel hairs. Where the so-treated web is used in manufacturing an absorbent article such as a diaper, the angel hairs can have an uncomfortable tackiness for the body of the wearer of such an absorbent article. The strung out adhesive can also cause problems elsewhere in the manufacturing process.

Another method of applying adhesive simply sprays adhesive onto a moving web close to, but without quite reaching a lateral edge of the web. This method generally avoids adhesive going beyond the lateral edge, but also prevents applying adhesive at the distal edge, such that bonding of the distal edge of the web to another web or workpiece is frustrated.

Other methods of applying adhesive require complex registration systems. These registration systems can use printed, intermittent or oscillating, or other applicators to apply adhesive to a web.

Prior methods of applying chemicals to a web of material include utilizing a stencil between a chemical applicator and the web. In this manner, a defined surface area of the web of interest is covered by the chemicals. U.S. Pat. No. 5,415,717 to Pemeborn shows an example of a stencil belt controlling the placement of particles onto an underlying web. There is no disclosure of applying adhesives or applying the particles at the lateral edge of the underlying web.

U.S. Pat. Nos. 5,094,886 and 4,968,534 to Bogardy disclose methods and apparatus for impregnating the surface of a web with a liquid in the form of a pattern. Stencil pattern belt 211 is located between the web and the liquid applicator. This device would not work with hot melt adhesives because the adhesives would build up on the stencil belt and make the device inoperative over a short period of time. Further, there is no disclosure of applying adhesives at the lateral edge of the underlying web.

U.S. Pat. No. 5,501,149 to Schleinz et al disclose a dual substrate printing system. A printed substrate is located between an ink printing station and a backing substrate. The backing substrate receives ink that strikes through the printed substrate. Thus two ink patterns are formed. Column 4, lines 31–42 disclose registration of ink patterns. Registration is not needed or desired for the invention described herein. Further, there is no disclosure of applying adhesives in Schleinz et al, including not at the lateral edges of the printed substrate.

None of the art discloses having a second web in surface-to-surface relationship with a first web and extending outwardly from a lateral edge of the first web, and then applying adhesive at the lateral edge of the first web, some adhesive being received on the second web outwardly of the lateral edge of the first web.

SUMMARY OF THE DISCLOSURE

The invention comprises methods of applying adhesive to an edge of a web of material. One method comprises the steps of transporting, along a first path, a first web of material having a lateral edge extending along the first path, transporting a second web of material along a second path, the second web facing the first web in surface-to-surface relationship with the first web at the lateral edge, and extending outwardly beyond the lateral edge. The method further includes applying adhesive to the first web at the lateral edge, at least some adhesive passing outwardly of the lateral edge, adhesive passing outwardly of the lateral edge, and thus outwardly of the first web, being received on the second web adjacent the lateral edge of the first web. The first and second webs are separated after adhesive is applied to the first web.

The method can include having a third web facing the first web in surface-to-surface relationship with the first web at the second lateral edge, and extending outwardly beyond the second lateral edge of the first web. The method can include the steps of transporting the third web along a third path, and separating the third web from the first web. The first, second and third webs can comprise respective substrates.

In some methods, the step of applying adhesive to the first web includes applying adhesive to the first web at the second lateral edge, at least an outer portion of the adhesive passing outwardly of the second lateral edge, and thus outwardly of the first web, the outer portion of the adhesive being received on a third web adjacent the second lateral edge.

In some embodiments, the adhesive comprises a composition which at least partially solidifies after the adhesive is applied to the first web, the separating of the second web from the first web occurring before significant solidification of the adhesive. To that end, the separating step may occur less than about 3 seconds after adhesive is applied to a respective portion of the first web. The separation of the second web from the first web thus forms a clean distal edge at the lateral edge of the first web.

In preferred methods, a hot melt adhesive is sprayed onto the webs. Prompt separation of the second web from the first web effectively avoids formation of angel hairs extending from the lateral edge of the first web.

Other methods of the invention are similar, except for periodic spaced cut-outs at a lateral edge of a first web. Adhesive is then applied to the first web at the lateral edge, including at spaced locations corresponding to the spaced cut-outs.

In some methods, such as those having no third web, the first and second webs have respective first and second widths, the second width being greater than the first width. Thus, the second web can concurrently extend outwardly beyond both respective lateral edges of the first web, at least at the spaced cut-outs.

In some methods, the lateral edge comprises a first lateral edge, the spaced cut-outs comprise first spaced cut-outs, the first web has a second opposing lateral edge, and the second lateral edge has second spaced cut-outs. A third web faces the first web in surface-to-surface relationship with the first web at the second lateral edge, and extends outwardly from the second lateral edge at least at the second spaced cut-outs. The third web receives adhesive passing outwardly of the second lateral edge.

In some methods, the first and second webs are transported and adhesive applied without ongoing longitudinal registration of the second web with respect to the first web.

In another embodiment of the invention, the method includes the steps of transporting a first web of material along a first path, periodically cutting leg cut-outs at spaced locations along opposing first and second lateral edges of the first web, transporting a second web of material along a second path, the second web facing the first web in surface-to-surface relationship with the first web at least at one of the first and second lateral edges, applying adhesive to the first web, at least some of the adhesive passing outwardly of at least one of the first and second lateral edges, adhesive passing outwardly of a lateral edge of the first web being received on the second web adjacent the respective one of the first and second lateral edges, separating the first and second webs, and securing the first web to a product forming web to form the product substrate.

The manufacture of an article utilizing elements from the first web having adhesive thereon, and elements from the second web having adhesive thereon is a further part of the invention. For instance, the first web can be utilized to manufacture a product substrate. The product substrate, in combination with elements from the second web having adhesive thereon, can be used to manufacture an article.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. None of the drawings are drawn to scale. The size or width of elements may be enlarged for purposes of illustration.

DETAILED DESCRIPTION OF THE ILLUSTRATED EMBODIMENTS

The present invention is directed toward methods for applying adhesive to a lateral edge of a first web of material. A second web of material is placed adjacent and in surface-to-surface relationship with the first web of material at the lateral edge. An adhesive applicator then applies adhesive to the lateral edge of the first web. The second web receives and retains adhesive which passes outwardly of the lateral edge of the first web. The second web is then turned away from the first web so that the clean distal edge of the first web retains adhesive without development of angel hairs at the distal edge.

Figure 1:
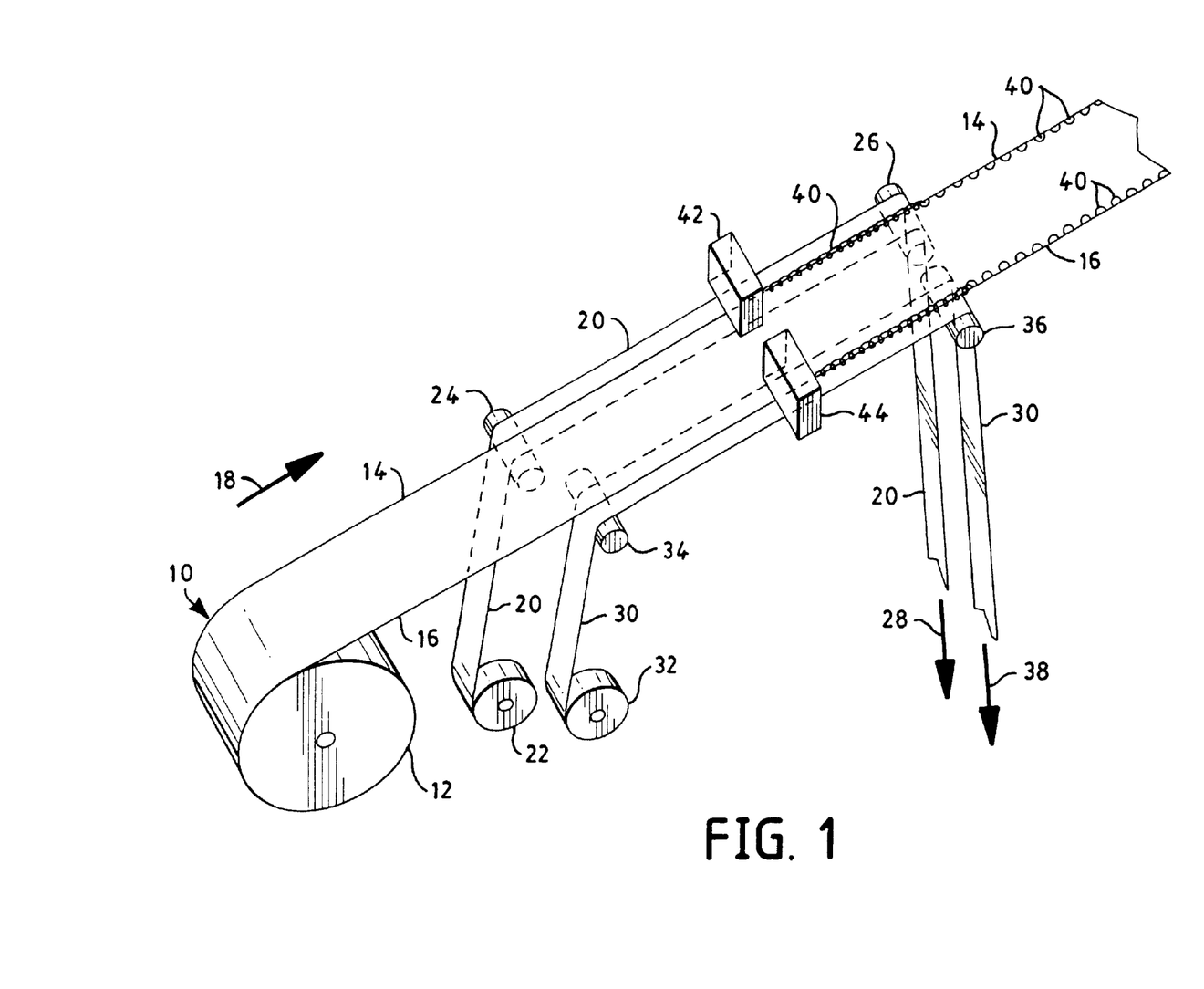
FIG. 1 shows a pictorial view of a first web of material receiving adhesive at its first and second lateral edges, with second and third webs underlying and extending outwardly from respective lateral edges of the first web.

FIG. 1 shows an assembly for applying adhesive to a first web 10 of material, comprising a first substrate, and supplied from supply roll 12. First web 10 has first lateral edge 14 and second opposing lateral edge 16 extending along the length of web 10. First web 10 moves along a first path in the direction shown by arrow 18.

Second web 20 of material comprising a second substrate from second supply roll 22 turns about first and second turning rolls 24, 26, and travels in a substantially straight second path between turning rolls 24, 26 in substantially the same direction as first web 10. Between first and second turning rolls 24, 26, second web 20 faces first web 10 in surface-to-surface relationship with the first web, and extends outwardly beyond first lateral edge 14 as shown in FIG. 1. From turning roll 26, second web 20 moves downwardly in the direction of arrow 28 after turning about second turning roll 26.

A third web 30 of material comprising a third substrate from third supply roll 32 is disposed at substantially the same angles and positions as second web 20, as applied at second lateral edge 16 of first web 10. Thus third web 30 turns about third and fourth turning rolls 34, 36 and travels in a substantially straight third path between turning rolls 34, 36. Between third and fourth turning rolls 34, 36, third web 30 faces first web 10 in surface-to-surface relationship with the first web, and extends outwardly beyond second lateral edge 16. From such face-to-face relationship, turning roll 36 guides third web 30 downwardly in the direction of arrow 38. Adhesive 40 is applied by adhesive applicators 42, 44, for example, in a swirling pattern as shown in FIG. 1. Since the purpose of the operation illustrated in FIG. 1 is to apply adhesive at and adjacent lateral edges 14, 16 of web 10, some, and preferably most, of adhesive 40 is received at and adjacent lateral edges 14, 16, and remains at such locations on first web 10, while an outer portion of the adhesive comprising overspray from applicators 42, 44 passes outwardly of lateral edges 14, 16 and is received and retained on webs 20, 30.

Web 10 of material may be a web which can be used to make outer covers for absorbent articles for receiving human exudates, such as diapers. Thus web 10 is typically substantially impermeable to liquids. Such web 10 can be formed from a single layer, or from multiple components, layers, or partial layers, of material.

Web 10 may be manufactured from a wide selection of web materials, such as polyolefin films, porous foams, reticulated foams, apertured plastic films, or one or more layers made with natural fibers. A typical web 10 may be manufactured from a thin plastic film or other flexible liquid-impermeable material. For example, first web 10 can be formed from a polyethylene film having a thickness of from about 0.012 millimeters to about 0.051 millimeters.

When it is desirable that first web 10 have a more clothlike feeling, the web may comprise a polyethylene film laminated to a nonwoven web, such as a spunbonded web of polyolefin fibers. For example, a polyethylene film having a thickness of about 0.015 millimeters may have thermally or otherwise laminated thereto a spunbonded web of polyolefin fibers having a thickness from 1.5 to 2.5 denier per filament, which nonwoven web has a basis weight of about 24 grams per square meter.

Various woven and nonwoven fabrics can be used for web 10. For example, web 10 may be composed of a meltblown or spunbonded web of polyolefin fibers. Web 10 may also comprise a carded and/or bonded web composed of natural and/or synthetic fibers. Further, web 10 can be formed of a woven or nonwoven fibrous web which has been constructed or treated, in whole or in part, to impart a desired level of liquid impermeability to selected regions of the web.

Web 10 may be composed of a substantially hydrophobic material wherein the hydrophobic material is treated with a surfactant or otherwise processed to impart a desired level of wettability and hydrophilicity. Still further, first web 10 may optionally be composed of a micro-porous material which permits vapors to escape through the web while preventing human liquid exudates from passing through the web.

Web 10 can also comprise a bodyside liner for the above described absorbent article. For example, first web 10 may comprise wood or cotton fibers. Other possible materials are synthetic fibers, such as polyester or polypropylene fibers, or a combination of natural and synthetic fibers.

Web 10 may be formed from a single layer, or may comprise a multiplicity of components, layers, or partial layers, which correspond to any of the materials disclosed herein, as well as others known in the art.

In a particular embodiment of the present invention, web 10 may comprise a spunbonded polypropylene fabric composed of about 2.8–3.2 denier fibers formed into a web having a basis weight of about 22 grams per square meter and a density of about 0.06 grams per cubic centimeter. A preferred fabric is treated with about 0.3 weight percent of a surfactant.

Second web 20 can comprise any of the materials described above as potentially comprising first web. Furthermore, second web 20 can comprise, for example, a laminate including first and second outer nonwoven facing layers on opposing sides of an elastomeric core layer, the elastomeric core layer comprising a thermoplastic elastomeric composition such as a styrene ethylene butylene styrene terpolymer.

Second web 20 can also comprise a plurality of elastomeric elements comprising strands, ribbons or the like secured in a stretched condition to a nonelastomeric substrate, the elastomeric elements extending along the length of the nonelastomeric substrate.

Examples of other materials of which second web 20 may be comprised include, without limitation, spandex, nonwoven laminated webs, extruded elastomeric webs or meltblown webs, cross-machine direction stretchable web materials made with stretchable nonwovens, stretchable foam webs, and the like.

Figure 2:
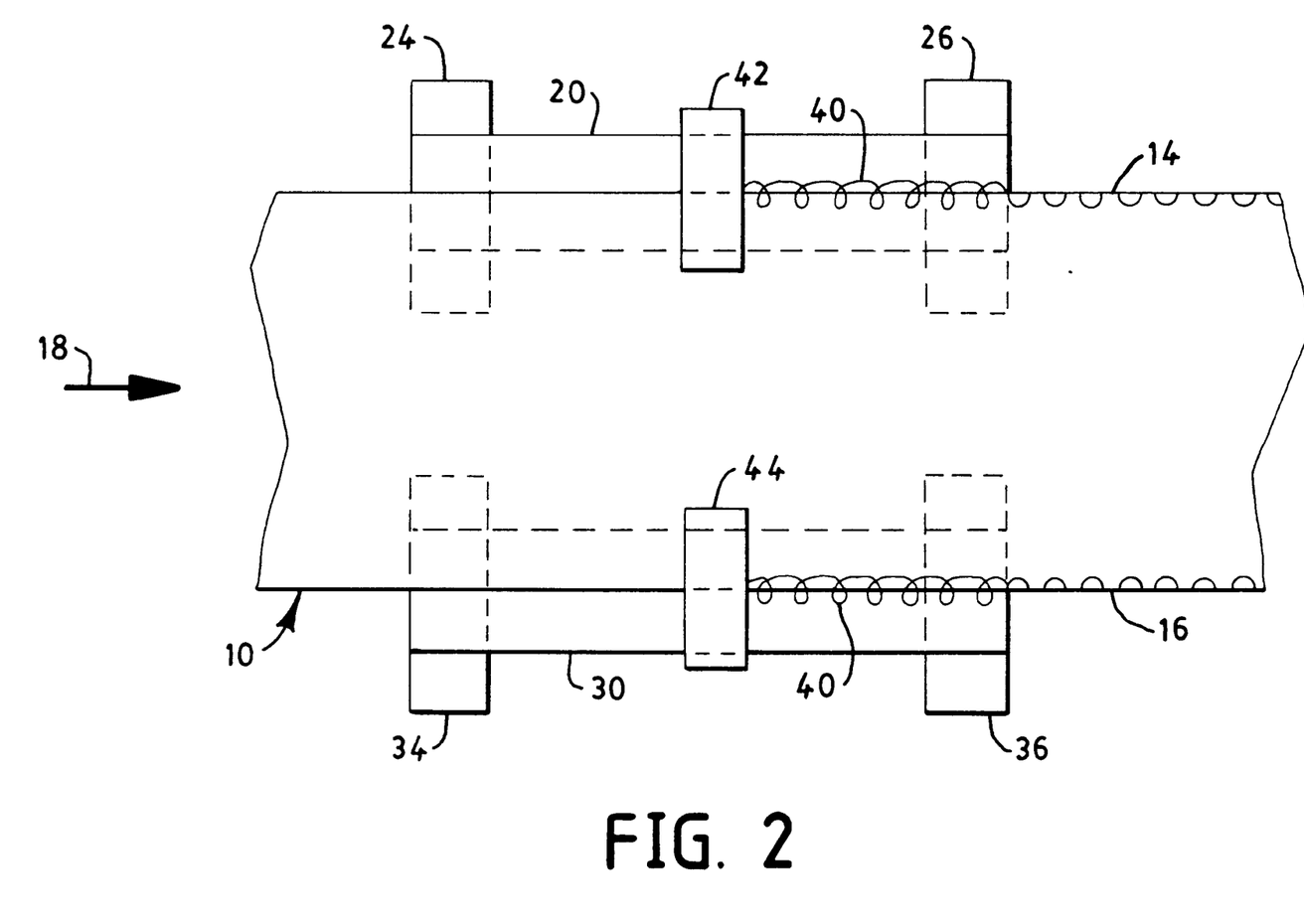
FIG. 2 shows a top view of the embodiment of FIG. 1.

Turning rolls 24 and 26, in combination, guide second web 20 in surface-to-surface relationship with first web 10 between the respective turning rolls. Surface-to-surface relationship is defined as being in close proximity to, and preferably in physical contact with, a portion of the surface of another web. A portion of the width of second web 20 extends outwardly from first lateral edge 14 of first web 10 as shown in FIGS. 1 and 2. First and second webs 10, 20 are in substantially the same plane, except first web 10 is positioned above second web 20, and between web 20 and adhesive applicator 42.

Turning rolls 34 and 36, in combination, guide third web 30 in surface-to-surface relationship with first web 10 between the respective turning rolls. A portion of the width of third web 30 extends outwardly from second lateral edge 16 of first web 10 as shown in FIGS. 1 and 2. First and third webs 10, 30 are in substantially the same plane, except first web 10 is positioned above third web 30 and between web 30 and adhesive applicator 44. Spacing between webs 10 and 20, and between webs 10 and 30, is acceptable so long as the spacing is limited such that the adhesive overspray from applicators 42, 44 is effectively received and retained by webs 20 and 30.

Turning rolls 24, 26, 34, 36 can comprise standard anvil rolls, idler rolls or other rolls well known in the art. The speed of first, second, and third webs 10, 20, 30 can be controlled elsewhere by driven rolls, by winders, or by other driven or driving devices. While second and third webs 20, 30 underlying first web 10 can be driven at speeds 20% greater than the speed of the first web, the first, second, and third webs preferably are driven at substantially the same speeds along the respective first, second and third paths in substantially the same direction between the respective turning rolls.

Adhesive applicator 42 applies an exemplary swirling pattern of adhesive 40 toward first and second webs 10, 20. While only a single applicator 42 having a single nozzle to form the swirling pattern is shown in FIG. 1, any number of applicators having any number of nozzles can be utilized to apply adhesive 40. For example, an adhesive applicator 42 with three nozzles can be utilized to provide the adhesive pattern shown in FIG. 4. Three adhesive applicators can also be used instead of one applicator with three nozzles. One example of an adhesive applicator is set forth in U.S. Pat. No. 4,949,668 to Heindel et al, the disclosure of which is hereby incorporated by reference in its entirety. Heindel et al disclose apparatus for applying hot melt adhesive to a web in making an absorbent article.

Adhesive applicator 44 preferably sprays patterns of adhesive 40 toward first and third webs 10, 30. Adhesive applicator 44 can be the same as adhesive applicator 42 and as described in Heindel et al. A wide variety of other applicators, such as other spray applicators, printing or other patterned rolls or the like, and applying cold as well as hot adhesives are contemplated as being within the scope of the invention.

Adhesive 40 can comprise a composition which at least partially solidifies after the adhesive is applied to the respective web. In that regard, adhesive 40 preferably comprises a hot melt adhesive. Suitable adhesives include, for example, 34-5522 or 34-5510 adhesive supplied by National Starch and Chemical Corp., or other hot-melt adhesives or adhesive compositions having similar properties. Furthermore, water soluble ethylene vinyl acetate adhesives, or other adhesives with appropriate characteristics can be utilized.

While FIG. 1 shows a generally continuous, semi-cycloidal swirl pattern for adhesive 40, other patterns can be utilized. For instance, zig-zag patterns, straight line patterns, an overall pattern, and other continuous or discontinuous patterns can be used so long as requisite amounts of adhesive are applied in acceptable patterns.

In operation, first web 10 is drawn from supply roll 12 by any of a wide variety of conventional driven devices (not shown) such as a driven roll. Similarly, second and third webs 20 and 30 are drawn from second and third supply rolls 22, 32 by any of a wide variety of conventional driven devices (not shown) such as driven rolls.

Turning roll 24 turns second web 20 at a location adjacent and extending outwardly from first lateral edge 14 of first web 10. Turning rolls 24 and 26, in combination, position second web 20 in surface-to-surface relationship with first web 10, and guide web 20 in substantially the same direction as first web 10 and along a second path closely adjacent the first path traversed by web 10. Turning roll 26 then turns second web 20 downwardly in direction 28 for further usage in the manufacturing process.

While second web 20 is between first and second turning rolls 24, 26, adhesive 40 is applied by adhesive applicator 42. Adhesive 40 is generally projected toward and received on web 10 at and adjacent lateral edge 14. With the spray pattern being specifically directed at the lateral edge, some of the adhesive passes outwardly of lateral edge 14, and is received on and adheres to second web 20. Thus, second web 20 receives the overspray that is inherent in projecting a spray pattern at lateral edge 14. Second web 20 thus protects and shields web handling machinery underlying web 20 from adhesive 40.

Figure 3:
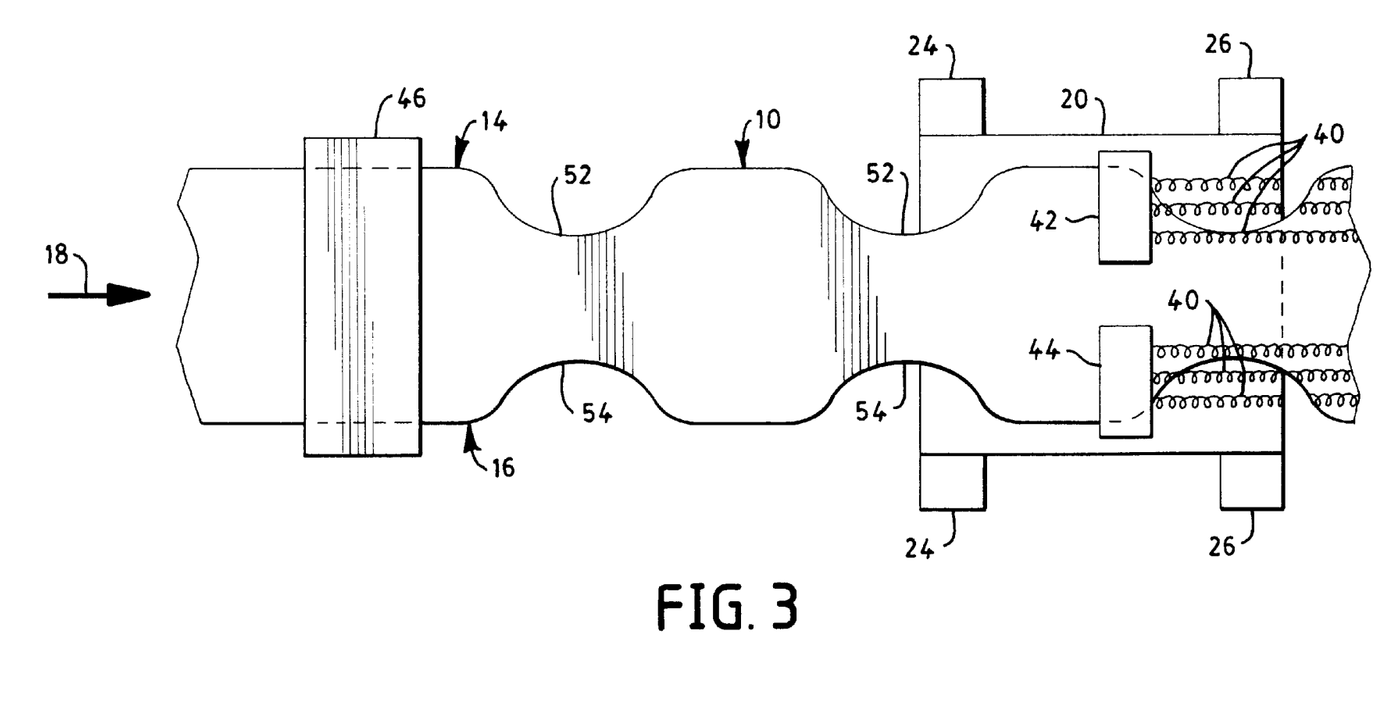
FIG. 3 shows a top view of a second embodiment of the invention, including a cut-out device making leg cut-outs on the first web.

As illustrated in FIGS. 1–3, adhesive is applied to at least one of the webs 10, 20 and 30 over less than the entirety of the respective surface thereof.

In terms of applying adhesive, if the overspray is being minimized, zones along the edge of second and third webs 20, 30, comprise the entire area where adhesive 40 overspray is received on webs 20, 30 from applicators 42, 44. These overspray zones can have a width of about two centimeters, but preferably within about 1 centimeter.

Intentional overspray of adhesive 40 is contemplated, when necessary, to secure second and/or third web 20, 30 elsewhere in the process. Furthermore, other nozzles (not shown) can be utilized to completely cover first web 10 with adhesive 40 for securement to another web, substrate or the like.

While FIGS. 1 and 2 show second web 20 underlying a portion of first web 10 and adhesive applicator 42 above first and second webs 10, 20, all of their positions can be reversed such that adhesive applicator 42 is below the webs pointing upwardly, and second web 20 is above first web 10. The relative three dimensional ordering of first and second webs 10, 20 and adhesive applicator 42 relative to each other is critical, but their three dimensional spatial arrangement with respect to a reference surface such as a horizontal surface is not critical since properly oriented adhesive applicators can direct a spray in any desired direction, at any angle without limitation.

Referring again to FIGS. 1 and 2, after adhesive 40 is sprayed onto webs 10, 20, second turning roll 26 turns second web 20 downwardly and away from first web 10. This turning operation separates second web 20 from first web 10. The turning operation or separating step occurs before significant solidification of the adhesive. Since the preferred adhesive is a hot melt adhesive, and since hot melt adhesives may cool rapidly upon application to web 10, the turning of web 20 away from web 10 as at roll 26 generally occurs less than about 3 seconds after adhesive 40 is applied to the respective portion of first web 10, namely before the hot melt adhesive solidifies significantly. Since second web 20 separates from web 10 before the hot melt adhesive solidifies, namely while the hot melt adhesive is quite liquidous, any adhesive bridging webs 10, 20 at lateral edge 14 separates into respective elements thereof on the respective webs while still in liquid form. Thus, the separation occurs cleanly, without creation of strings, or angel hairs, between the two webs as the webs separate. Such clean separation leaves distal edge 14 similarly clean and free from such angel hairs.

Clean distal edge is defined as a lateral edge having no, or substantially no, angel hairs formed by the adhesive. If, on the other hand, the hot melt adhesive is allowed to cool and thus become more viscous before separation of web 20, angel hairs may be formed by the hot melt adhesive stringing outwardly along the lateral edge of a web as the webs are separated. These angel hairs generally are too viscous to break clean from the web. Angel hairs generally are very fine and can be up to about two feet in length. A final product, such as an absorbent article having angel hairs is aesthetically unattractive, and functionally less desirable because of the angel hairs.

Turning roll 34 turns third web 30 at a location adjacent and extending outwardly from second lateral edge 16 of first web 10. Turning rolls 34 and 36, in combination, position third web 30 in surface-to-surface relationship with first web 10, and guide web 30, in substantially the same direction as first web 10 and along a third path closely adjacent the first path traversed by web 10. Turning roll 36 then turns third web 30 downwardly in direction 38 for further usage in the manufacturing process.

Third web 30, turning rolls 34, 36 and second adhesive applicator 44 operate in essentially the same way as second web 20, turning rolls 24, 26, and adhesive applicator 42 to apply adhesive to second lateral edge 16 of first web 10.

An important operating feature of the invention is the lack of any need for longitudinal registration. Therefore, there is no need for any particular longitudinal positioning between first, second, and third webs 10, 20, 30.

While FIGS. 1 and 2 show second and third webs 20, 30 at respective lateral edges of first web 10, the invention broadly contemplates applying adhesive 40 to only one lateral edge in some embodiments. In such instance, third web 30 and second adhesive applicator 44 are not required.

The adhesive applied to first web 10 can be used to secure other webs or other elements to web 10 in a manufacturing process. An article can be formed utilizing elements e.g. severed from first web 10, the severed elements having adhesive 40 thereon. Such article can include elements from second web 20 having adhesive 40 thereon as well as third web 30 in some instances. One class of products desirably made with the adhesive-coated webs made with the methods of the invention is absorbent articles for receiving and retaining body exudates, for example diapers.

While the method of applying adhesive to lateral edge 14 of first web 10 is generally disclosed for use in manufacturing absorbent articles, the method can be used to adhere pieces of apparel, sheets, and any other substrate materials to one another.

The embodiment shown in FIGS. 1 and 2 can be modified so that a single second web 20 extends both beyond first lateral edge 14 and beyond second lateral edge 16. In this embodiment, second web 20 has a greater width than first web 10, thus obviating the need for web 30. This arrangement is similar to the embodiment of FIGS. 3 and 4 described in more detail hereinafter, except for the leg cut-outs.

While FIG. 1 shows supply roll 12 feeding first web 10 toward adhesive applicators 42, 44 and second and third webs 20, 30 similarly being fed toward adhesive applicators 42, 44, other manufacturing steps can operate on any or all of such webs before the respective webs reach the adhesive applicators. For example, attachment ears or other elements can be secured to first web 10 before web 10 reaches second and third webs 20, 30. Thus, the invention is not limited in the order or amount of steps taking place in the manufacturing process, either before, during, or after application of adhesive 40.

Figure 4:
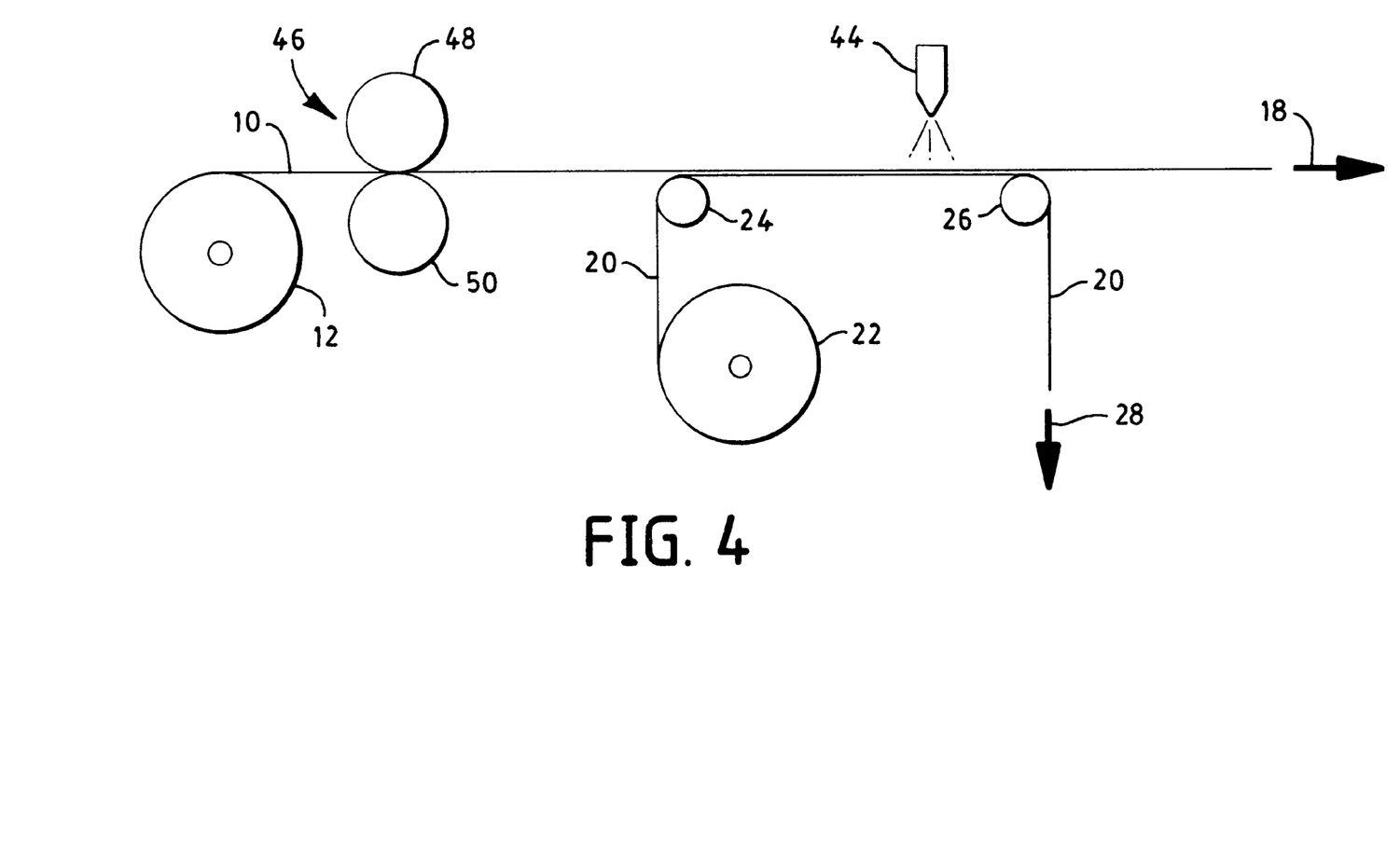
FIG. 4 shows a side view of the embodiment shown in FIG. 3.

FIGS. 3 and 4 show a second embodiment of the invention. In this embodiment, first web 10 from supply roll 12 passes through die cutter 46 before reaching turning roll 24.

Die cutter 46 comprises an anvil roll 48 and a knife roll 50. Die cutter 46 forms periodic, opposing spaced leg cut-outs 52, 54 in first web 10 as shown in FIG. 3. First web 10 having opposing leg cut-outs 52, 54 then advances along the first path to a locus adjacent turning rolls 24, 26.

In this embodiment, turning rolls 24, 26 extend across the width of first web 10, and outwardly of lateral edges 14, 16 of web 10 at least at cut-outs 52, 54. Turning rolls 24 and 26, in combination, guide second web 20 of material in surface-to-surface relationship with first web 10, as defined earlier. The relationship wherein web 20 receives and retains overspray of adhesive 40 at edges 14, 16 occurs between turning rolls 24, 26. Turning roll 26 then turns second web 20 away from first web 10. In this embodiment, second web 20 has a greater width than first web 10 and extends outwardly therefrom at least at leg cut-outs 52, 54, and may extend outwardly of web 10 at the greatest widths of web 10 as shown in FIG. 3.

As in the earlier embodiments, turning rolls 24, 26 can comprise standard anvil rolls, idler rolls, or other rolls well known in the art. Similarly, the speed of first and second webs 10, 20 can be controlled elsewhere by driven rolls, by winders, or by other driven or driving devices. First and second webs 10, 20 preferably are driven at substantially the same speeds along the respective first and second paths in substantially the same direction between the respective turning rolls.

First web 10 and second web 20 can comprise the materials disclosed in the first embodiment. First web 10 preferably comprises outer cover material for an absorbent article such as a diaper, feminine napkin, training pants or the like. Second web 20 can comprise any of the materials disclosed earlier with respect to the first embodiment of the invention.

Instead of having a single nozzle as shown in the embodiment of FIGS. 1 and 2, adhesive applicator 42 can comprise an applicator having multiple nozzles or multiple applicators. A swirl pattern of adhesive 40 as shown in FIG. 3 or other adhesive patterns can be directed toward first and second webs 10, 20.

Die cutter 46 is shown as a combination of anvil roll 48 and knife roll 50. A variety of known cutter devices are acceptable for cutting leg cut-outs 52, 54. In all such cutter devices, the cutting loci effectively move inwardly and outwardly while first web 10 passes through the respective cut-out device to form the shaped leg cut-outs 52, 54.

In operation, the embodiment of FIGS. 3 and 4 receives first web 10 at die cutter 46. Knife roll 50, in combination with anvil roll 48, cuts out leg cut-outs 52, 54 at spaced distances or intervals as shown in FIG. 3.

Second web 20 leaves second supply roll 22 and advances to first turning roll 24. First turning roll 24 directs second web 20 toward second turning roll 26 facing the first web in surface-to-surface relationship with, and preferably in physical contact with, first web 10. Second web 20 extends outwardly of the first web at lateral edges 14, 16 at least at leg cut-outs 52, 54 and can extend outwardly beyond lateral edges 14, 16 at the widest portions of first web 10, such as between leg cut-outs 52 or between leg cut-outs 54, or both.

Lateral edges 14, 16 of first web 10 have adhesive 40 applied by adhesive applicators 42, 44. In terms of applying adhesive 40, each lateral edge defines a zone along the edge including at cut-outs 52, 54 of web 10. This zone can comprise the entire area where adhesive 40 is applied in FIGS. 3 and 4. This zone extends inwardly from the innermost edge 14 or 16 at leg cut-outs 52, 54 and can extend outwardly beyond lateral edges 14, 16 in areas away from leg cut-outs 52.

Adhesive 40 can be applied continuously at one or more locations between first turning roll 24 and second turning roll 26.

Some of adhesive 40 reaches second web 20 along leg cut-outs 52, 54. Much of the adhesive remains on first web 10 at the edge of leg cut-outs 52, 54 as well as along the entireties of lateral edges 14, 16. However, adhesive 40 could be applied intermittently only in the regions of leg cut-outs 52, 54 if desired. Intermittent application of adhesive 40, however, would require registration of leg cut-outs 52, 54 with operation of adhesive applicators 42, 44. Therefore, intermittent operation is not preferred.

After application of adhesive 40, turning roll 26 then directs second web 20 downwardly away from first web 10. This step separates second web 20 from first web 10 while the adhesive is still highly liquidous. Thus, the turning or separating step occurs before significant solidification of the adhesive. Thus, the turning step preferably occurs less than about 3 seconds after adhesive 40 is applied to a respective portion of first web 10.

Due to the quick removal of second web 20, opposing leg cut-outs 52, 54 of first web 10 have clean distal edges with no angel hairs or adhesive 40 extending outwardly from the edge of the respective leg cut-out, as described for the previous embodiment. In use, second web 20 receives the overspray adhesive 40 at lateral edges 14, 16, thus protecting and shielding underlying machinery from the adhesive.

The adhesive on first web 10 can be used to secure the first web to a product forming web in a manufacturing process (not shown) to form a product substrate (not shown). A product forming web can, for example, comprise leg cuff material, an absorbent core, a bodyside liner or the like.

The product forming web can also comprise a substrate that can be arranged to pass under, in surface-to-surface relationship with a first web comprising an outer cover such that overspray of adhesive sprayed at leg cut-outs, for instance, is received by the substrate. The substrate can then be used to form part of the chassis of an absorbent article. Thus, the substrate can be used to prevent contamination of absorbent article fabrication machinery and can then be used as a base structure for the chassis. The substrate can be directed as needed by turning rolls to travel to other areas of an apparatus. In such an apparatus, first web 10 comprises an outer cover including attachment ears and second web 20 comprises the substrate.

Referring, now to the instant invention, other arrangements are also contemplated. For instance, first web 10 can comprise a bodyside liner, absorbent core, or the like. First web 10 can also be used as a substrate for other products such as apparel, blankets, or the like, or as a layer to be applied to substrates of such products.

Figure 5:
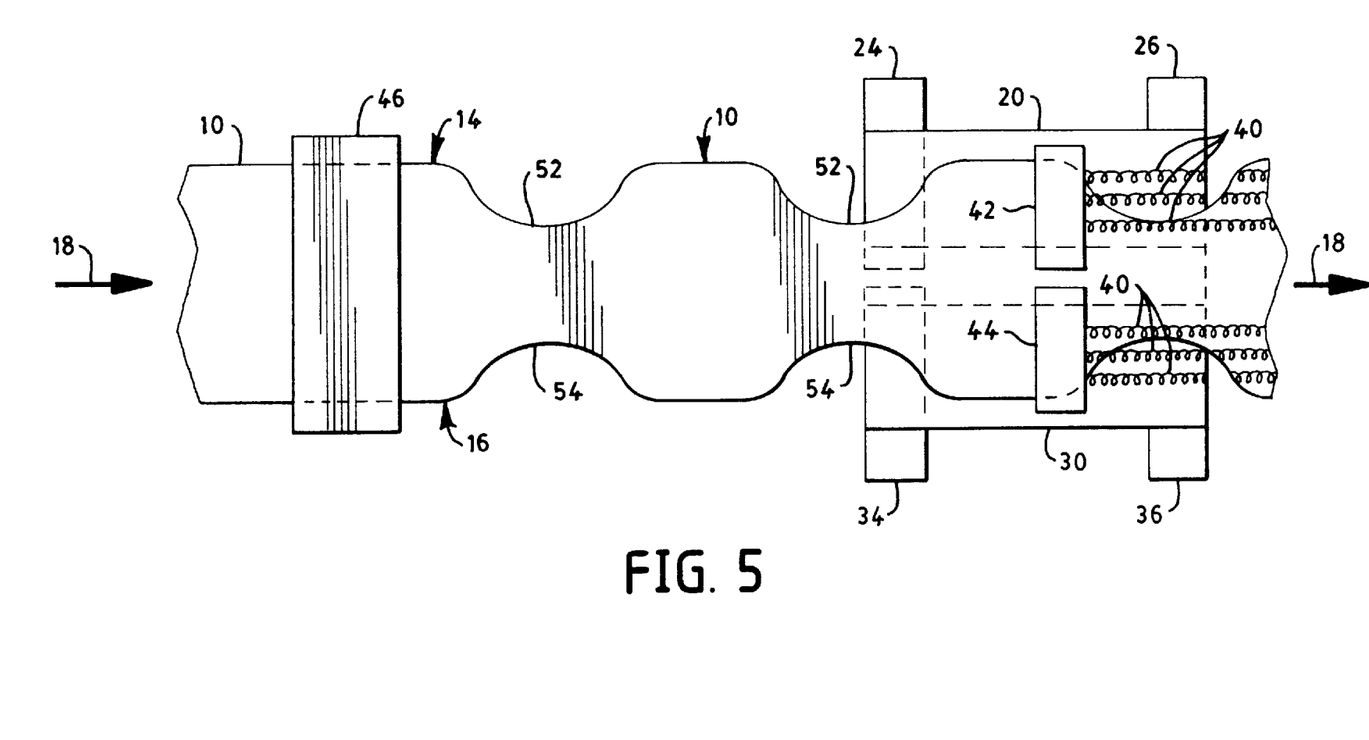
FIG. 5 shows a top view of a third embodiment similar to that of FIG. 3, except second and third webs are disposed in face-to-face relationship with the first web at respective first and second lateral edges of the first web.

FIG. 5 is a further embodiment, combining the leg cut-outs shown in FIGS. 3 and 4 with the two underlying webs 20, 30 shown in FIGS. 1 and 2.

In operation, the assembly of FIG. 5 operates essentially the same way as the embodiment of FIGS. 3 and 4. The main difference is that third web 30 replaces the function of second web 20 at second lateral edge 16 and leg cut-outs 54.

Second web 20 and/or third web 30 can be combined or utilized as described earlier to create a substrate, absorbent article chassis or the like.

While the above invention is used mainly to form absorbent articles or the like, other applications are contemplated.

For instance, the invention can be utilized to form disposable garments, clothes, or other products. Therefore, the invention is not limited to absorbent articles or the health care field.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. A method of applying adhesive to at least three webs of material, the method comprising the steps of:
   (a) transporting a first web of material along a first path, the first web of material comprising a first substrate having first and second opposing surfaces, and first and second opposing lateral edges extending along the first path;
   (b) transporting a second web of material along a second path, the second web of material comprising a second substrate having third and fourth opposing surfaces, the third surface facing the first web of material in surface-to-surface relationship with the second surface of the first web of material at the first lateral edge, and extending outwardly beyond the first lateral edge;
   (c) transporting a third web of material along a third path, the third web of material comprising a third substrate having fifth and sixth opposing surfaces, the fifth surface facing the first web of material in surface-to-surface relationship with the second surface of the first web of material at the second lateral edge, and extending outwardly beyond the second lateral edge;
   (d) applying adhesive to the first web of material at the first lateral edge on the first surface, including applying at least some adhesive outwardly of the first lateral edge, adhesive passing outwardly of the first lateral edge, and thus outwardly of the first web of material, being received on the third surface of the second web of material adjacent the first lateral edge of the first web of material; and
   (e) applying adhesive to the first web of material at the second lateral edge on the first surface, including applying at least some adhesive outwardly of the second lateral edge, adhesive passing outwardly of the second lateral edge, and thus outwardly of the first web of material, being received on the fifth surface of the third web of material adjacent the second lateral edge of the first web of material, adhesive being thereby applied over less than the entireties of the respective surfaces of each of the webs of material.

2. A method as in claim 1, including the step of separating the first and second webs of material from each other less than about 3 seconds after adhesive is applied to a respective portion of the first web of material.

3. A method as in claim 1, including transporting the first, second, and third webs without ongoing longitudinal registration of the second web or the third web with respect to the first web.

4. A method as in claim 1, the adhesive comprising a composition which at last partially solidifies after the adhesive is applied to the first web of material, the method including separating the first and second webs of material before significant solidification of the adhesive.

5. A method as in claim 1, the applying of the adhesive comprising spraying the adhesive.

6. A method as in claim 5, the adhesive comprising a hot melt adhesive.

7. A method as in claim 6, use of the second and third webs effecting avoidance of the formation of angel hairs extending from the first and second lateral edges of the first web.

8. A method as in claim 6, including the step of separating the first and second webs of material from each other, the separating of the webs of material including separating the second web of material from the first web of material to form, at the lateral edge of the first web of material, a clean distal edge.

9. A method of applying adhesive to cut-outs of a web of material, the method comprising the steps of:
   (a) transporting a first web of material along a first paths the first web of material having first and second opposing surfaces, and periodic spaced cut-outs at a first lateral edge and a second opposing lateral edge along a length thereof;
   (b) transporting a second web of material along a second path, the second web of material having third and fourth opposing surfaces, the third surface facing the first web of material in surface-to-surface relationship with the second surface of the first web of material at the first lateral edge; and
   (c) applying adhesive to the first web of material at the first lateral edge on the first surface, at least some adhesive passing outwardly of the first lateral edge at spaced locations corresponding to the first spaced cut-outs, adhesive passing outwardly of the first lateral edge, and thus outwardly of the first web of material being received on the third surface of the second web of material adjacent the first lateral edge of the first web of material, adhesive being thereby applied over less than the entireties of the respective surfaces of each of the webs of material.

10. A method as in claim 9, the applying of the adhesive comprising spraying a hot melt adhesive.

11. A method as in claim 9, the adhesive comprising a composition which at last partially solidifies after the adhesive is applied to the first web of material, the method including separating the first and second webs of material before significant solidification of the adhesive.

12. A method as in claim 9, including the step of separating the first and second webs of material from each others the separating of the webs of material including separating the second web of material from the first web of material to form, at the lateral edge of the first web of material, a clean distal edge.

13. A method as in claim 9, the first and second webs having respective first and second widths, the second width being greater than the first width at the first and second spaced cut-outs, the step of applying adhesive to the first web at the second edge including at least some adhesive passing outwardly of the second lateral edge at spaced locations corresponding to the second spaced cut-outs, adhesive passing outwardly of the second lateral edge, and thus outwardly of the first web being received on the third web adjacent the second lateral edge of the first web.

14. A method as in claim 9, including utilizing the second web elsewhere in a related manufacturing process after the adhesive is received on the second web.

15. A method as in claim 9, including manufacturing an article utilizing elements from the first web having adhesive thereon, and elements from the second web having adhesive thereon.

16. A method as in claim 9, the first web comprising a first substrate, the second web comprising a second substrate, and a third web of material comprising a third substrate, the third web facing the first web in surface-to-surface relationship with the first web at the second lateral edge, and extending outwardly from the second lateral edge at the second spaced cut-outs.

17. A method as in claim 16, adhesive passing outwardly of the second lateral edge, and thus outwardly of the first web, being received on the third web adjacent the second lateral edge.

18. A method as in claim 9, including transporting the first and second webs through the step of applying adhesive, without ongoing longitudinal registration of the second web with respect to the first web.

19. A method of forming a product substrate, the method comprising the steps of:
 (a) transporting a first web of material along a first path;
 (b) periodically cutting leg cut-outs at spaced locations along opposing first and second lateral edges of the first web;
 (c) transporting a second web of material along a second path, the second web facing the first web in surface-to-surface relationship with the first web at least at one of the first and second lateral edges;
 (d) applying adhesive to the first web, at least some of the adhesive passing outwardly of at least one of the first and second lateral edges, adhesive passing outwardly of a respective lateral edge of the first web being received on the second web adjacent the respective one of the first and second lateral edges;
 (e) separating the first and second webs; and
 (f) securing the first web to a product forming web to form the product substrate.

20. A method as in claim 19, the applying of the adhesive comprising spraying a hot melt adhesive.

21. A method as in claim 19 wherein said product substrate comprises an absorbent article chassis.

22. A method as in claim 19, including manufacturing an article utilizing the product substrate and elements from the second web having adhesive thereon.

23. A method as in claim 19, the adhesive comprising a composition which at least partially solidifies after the adhesive is applied to the first web, the separating step occurring before significant solidification of the adhesive.

24. A method as in claim 19, the separating step occurring less than about 3 seconds after adhesive is applied to a respective portion of the first web.

25. A method as in claim 19, the separating of the webs including separating the second web from the first web to form, at the lateral edge of the first web, a clean distal edge.

26. A method as in claim 19, including transporting the first and second webs through the step of applying adhesive without ongoing longitudinal registration of the second web with respect to the first web.

27. A method as in claim 19, including transporting a third web of material along a third path, the third web facing the first web in surface-to-surface relationship with the first web at the second lateral edge, and extending outwardly beyond the second lateral edge of the first web.

28. A method as in claim 19, the second web extending outwardly beyond the first and second lateral edges of the first web.

29. A method as in claim 19, the applying of the adhesive comprising spraying the adhesive.

30. A method of manufacturing and thereby assembling an absorbent article chassis, including applying adhesive to an edge of a web of material, the method comprising the steps of:
 (a) transporting a first web of material along the first path, the first web of material comprising a first substrate having a first lateral edge and a second opposing lateral edge extending along the first path;
 (b) transporting a second web of material along a second path, the second web of material comprising a second substrate facing the first web of material in surface-to-surface relationship with the first web of material at the first lateral edge, and extending outwardly beyond the first lateral edge;
 (c) transporting a third web of material along a third path, the third web of material comprising a third substrate facing the first web of material in surface-to-surface relationship with the first web of material at the second lateral edge, and extending outwardly beyond the second lateral edge;
 (d) applying adhesive to the first web of material at the first lateral edge, including applying a t least some adhesive outwardly of the first lateral edge, adhesive passing outwardly of the first lateral edge, and thus outwardly of the first web of material, being received on the second web of material adjacent the first lateral edge of the first web of material;
 (e) applying adhesive to the first web of material at the second lateral edge, including applying at least some adhesive outwardly of the second lateral edge, adhesive passing outwardly of the second lateral edge, and thus outwardly of the first web of material, being received on the third web of material adjacent the second lateral edge of the first web of material; and
 (f) manufacturing the absorbent article chassis utilizing elements from each of the webs of material having adhesive thereon.

31. A method as in claim 30, the adhesive comprising a composition which at last partially solidifies after the adhesive is applied to the first web of material, the method including separating first and second webs of material before significant solidification of the adhesive.

32. A method as in claim 30, including the step of separating the first and second webs of material from each other less than about 3 seconds after adhesive is applied to a respective portion of the first web of material.

33. A method as in claim 30, including transporting the first and second webs of material without ongoing longitudinal registration of the second web of material with respect to the first web of material.

34. A method of applying adhesive to an edge of a web of material in the process of manufacturing an article, the method comprising the steps of:
 (a) transporting a first web of material along a first path, the first web of material comprising a first substrate having a first lateral edge and a second opposing lateral edge extending along the first path;
 (b) transporting a second web of material along a second path, the second web of material comprising a second substrate facing the first web of material in surface-to-surface relationship with the first web of material at the first lateral edge, and extending outwardly beyond the first lateral edge;
 (c) transporting a third web of material along a third path, the third web of material comprising a third substrate facing the first web of material in surface-to-surface relationship with the first web of material at the second lateral edge, and extending outwardly beyond the second lateral edge;
 (d) applying adhesive to the first web of material at the first lateral edge, including applying at least some adhesive outwardly of the first lateral edge, adhesive passing outwardly of the first lateral edge, and thus outwardly of the first web of material, being received on the second web of material adjacent the first lateral edge of the first web of material;

(e) applying adhesive to the first web of material at the second lateral edge, including applying at least some adhesive outwardly of the second lateral edge, adhesive passing outwardly of the second lateral edge, and thus outwardly of the first web of material, being received on the third web of material adjacent the second lateral edge of the first web of material, the adhesive thereby being applied over less than the entirety of a surface of the first web of material; and (f) assembling an article, utilizing each of the coated first, second, and third webs of material in the process of manufacturing the article.

35. A method as in claim 34, the adhesive comprising a composition which at last partially solidifies after the adhesive is applied to the first web of material, the method including separating the first and second webs of material before significant solidification of the adhesive.

36. A method as in claim 34, including the step of separating the first and second webs of material from each other less than about 3 seconds after adhesive is applied to a respective portion of the first web of material.

37. A method as in claim 34, including transporting the first and second webs of material without ongoing longitudinal registration of the second web of material with respect to the first web of material.

38. A method as in claim 34 wherein said article comprises an absorbent article chassis.

* * * * *

UNITED STATES PATENT AND TRADEMARK OFFICE
CERTIFICATE OF CORRECTION

PATENT NO. : 5,932,284
DATED : August 3, 1999
INVENTOR(S) : Gary Mack Reynolds

It is certified that error appears in the above-identified patent and that said Letters Patent is hereby corrected as shown below:

Claim 4, line 2, change "last" to --least--.
       Claim 9, line 3, change "paths" to --path--.
       Claim11, line 2, change "last" to --least--.
       Claim 12, line 2, change "others" to --other--.
       Claim 13, line 9, after "third" insert --surface of the second--.
       Claim 31, line 2, change "last" to --least--.
       Claim 35, line 2, change "last" to --least--.

Signed and Sealed this

Thirtieth Day of January, 2001

Attest:

Q. TODD DICKINSON

*Attesting Officer*    *Director of Patents and Trademarks*